United States Patent [19]

Chen et al.

[11] Patent Number: 5,259,974
[45] Date of Patent: Nov. 9, 1993

[54] N,N-BIS(PHOSPHONOMETHYL)-2-AMINO-1-PROPANOL, DERIVATIVES AND CORRESPONDING LOWER ALKYL ETHERS AND N-OXIDES THEREOF FOR HIGH PH SCALE CONTROL

[75] Inventors: Shih-Ruey T. Chen, Pittsburgh; Gary F. Matz, Carneige; Raymond J. Schaper, Pittsburgh, all of Pa.

[73] Assignee: Calgon Corporation, Pittsburgh, Pa.

[21] Appl. No.: 860,373

[22] Filed: Mar. 30, 1992

[51] Int. Cl.$^5$ .............................................. C02F 5/14
[52] U.S. Cl. .................................. 210/700; 210/701; 252/180
[58] Field of Search ................. 210/698–701; 252/180, 181

[56] References Cited

U.S. PATENT DOCUMENTS

| | | | |
|---|---|---|---|
| 2,358,222 | 9/1944 | Fink | 210/697 |
| 2,539,305 | 1/1951 | Hatch | 210/697 |
| 2,783,200 | 2/1957 | Crum et al. | 210/701 |
| 2,980,610 | 4/1961 | Ruchrwein | 210/698 |
| 3,285,886 | 11/1966 | Gunderson et al. | 210/701 |
| 3,434,969 | 3/1969 | Ralston | 210/700 |
| 3,463,730 | 8/1969 | Booth et al. | 210/701 |
| 3,514,476 | 5/1970 | Morita et al. | 260/429.9 |
| 3,518,204 | 6/1970 | Hansen et al. | 252/181 |
| 3,928,196 | 12/1975 | Persinski et al. | 252/180 |
| 3,965,027 | 6/1976 | Boffardi et al. | 252/180 |
| 4,080,375 | 3/1978 | Quinlan | 210/700 |
| 4,088,574 | 5/1978 | Quinlan | 210/700 |
| 4,457,847 | 7/1984 | Lorenc et al. | 210/698 |
| 4,640,793 | 2/1987 | Persinski et al. | 252/82 |
| 4,650,591 | 3/1987 | Boothe et al. | 210/700 |
| 4,671,888 | 6/1987 | Yorke | 252/180 |
| 4,931,189 | 6/1990 | Dhawan et al. | 210/700 |
| 4,936,987 | 6/1990 | Persinski et al. | 210/699 |
| 4,973,744 | 11/1990 | Hwa et al. | 562/12 |
| 5,069,798 | 12/1991 | Hwa et al. | 210/700 |

OTHER PUBLICATIONS

Wayplex 61-A P. A. Hunt Chemical Corp.
Briquest 221-50A Albright & Wilson Technical Bulletin.

Primary Examiner—Peter Hruskoci
Attorney, Agent, or Firm—Craig G. Cochenour; William C. Mitchell; Raymond M. Speer

[57] ABSTRACT

N,N-bis(phosphonomethyl)-2-amino-1-propanol, derivatives and corresponding lower alkyl ethers and N-oxides thereof possess high calcium tolerance and have been found to give excellent inhibition of the formation, deposition and adherence of scale-forming salts, especially calcium carbonate, under severe conditions which include elevated pH, high dissolved solids content, and high saturation levels of calcium carbonate.

8 Claims, No Drawings

N,N-BIS(PHOSPHONOMETHYL)-2-AMINO-1-PROPANOL, DERIVATIVES AND CORRESPONDING LOWER ALKYL ETHERS AND N-OXIDES THEREOF FOR HIGH PH SCALE CONTROL

BACKGROUND OF THE INVENTION

1. Field of the Invention

The present invention relates to compositions and methods for inhibiting the formation, deposition and adherence of alkaline earth metal scale deposits, especially calcium carbonate ($CaCO_3$) scale deposits, on metallic surfaces of aqueous systems, especially under conditions of high pH and high calcite concentration, e.g., those found in cycled up cooling tower systems, where those compositions are N,N-bis(phosphonomethyl)-2-amino-1-propanol, derivatives and corresponding lower alkyl ethers and N-oxides thereof.

Generally, calcium carbonate scale deposits are incrustation coatings which accumulate on the metallic surfaces of a water-carrying system through a number of different causes.

Various industrial and commercial water-carrying systems are subject to calcium carbonate scale formation problems. Calcium carbonate scale is of particular concern in heat exchange systems employing water, such as, for example, boiler systems, and once-through and open recirculating water cooling systems. Cooling towers are especially significant, particularly where severe conditions, including high pH and high calcite concentrations are encountered.

The water employed in these systems ordinarily will contain a number of dissolved salts, and the alkaline earth metal cation calcium is usually prevalent, as is the anion carbonate. The combination product of calcium cation and carbonate anion will precipitate from the water in which they are carried to form scale deposits when the concentration of the anion and cation comprising the reaction product, i.e., calcium carbonate, exceeds the solubility of the reaction product itself. Thus, when the concentrations of calcium ion and carbonate ion exceed the solubility of the calcium carbonate reaction product, a solid phase of calcium carbonate will form as a precipitate. Precipitation of the reaction product will continue until the solubility product concentrations of the constituent ions are no longer exceeded.

Numerous factors may be responsible for producing a condition of supersaturation for the reaction product calcium carbonate. Among such factors are changes in the pH of the water system, evaporation of the water phase, rate of heat transfer, amount of dissolved solids, and changes in the temperature or pressure of the system.

For cooling systems and similar heat exchange systems including cooling towers, the mechanism of scale formation is apparently one of crystallization of scale-forming salts from a solution which is locally supersaturated in the region adjacent the heating surface of the system. The thin viscous film of water in this region tends to become more concentrated than the remainder of the solution outside this region. Precipitation is also favored on the heat transfer surface because of the inverse solubility relationship of calcium carbonate. As a result, the solubility of the scale-forming calcium carbonate salt reaction product is first exceeded in this thin film, and crystallization of calcium carbonate scale results directly on the heating or heat exchange surface.

In addition to this, a common source of scale in boiler systems is the breakdown of calcium bicarbonate to form calcium carbonate, water and carbon dioxide under the influence of heat. For open recirculating cooling water systems, in which a cooling tower, spray pond, evaporative condenser, and the like serve to dissipate heat by evaporation of water, the chief factor which promotes calcium carbonate scale formation is concentration of solids dissolved in the water by repeated evaporation of portions of the water phase. Thus, even a water which is not scale forming on a once-through basis usually will become scale forming when concentrated two, four, or six times. Moreover, alkalinity of the makeup water, with evaporative cycles over time results in an increasing alkalinity of the water in the overall system, often reaching pH's of 8.5-9.5 and even higher. Conventional scale inhibiting compositions typically fail in systems having such severe conditions.

The formation of calcium carbonate scale deposits poses a serious problem in a number of regards. The calcium carbonate scale which is formed possesses a low degree of heat conductivity. Thus, a calcium carbonate scale deposit is essentially an insulating layer imposed across the path of heat travel from whatever source to the water of the system. In the case of a cooling system, the retarded heat transfer causes a loss in cooling efficiency. In addition to this problem, calcium carbonate scale formation facilitates underdeposit corrosive processes, and a substantial calcium carbonate scale deposit will interfere materially with fluid flow. Consequently, calcium carbonate scale is an expensive problem in many industrial water systems, causing delays and shutdowns for cleaning and removal.

Although the present invention is directed primarily to preventing or inhibiting the deposition of calcium carbonate scale, the most prevalent type of scale deposit, it is also applicable to inhibiting the deposition of other types of alkaline earth metal scales, especially where those are associated with calcium carbonate scale under the severe conditions described herein. For example, most industrial and commercial water contains alkaline earth metal cations, such as calcium and magnesium, and several anions such as bicarbonate, carbonate, and phosphate. When combinations of these anions and cations are present in concentrations which exceed the solubility of their reaction products, precipitates form until their product solubility concentrations are no longer exceeded. These precipitates are alkaline earth metal scales. Thus, by alkaline earth metal scales is meant scales including but not limited to calcium carbonate, magnesium carbonate, and calcium phosphate. These scales form frequently in the tubes of heat exchangers and on other heat exchange surfaces, such as those in cooling towers. Particular systems or applications areas where severe conditions lead to exceptional buildup of calcium carbonate and related scales, in addition to cycled up cooling towers, include reverse osmosis systems, sugar refining evaporators, and certain types of gas scrubbers.

The N,N-bis(phosphonomethyl)-2-amino-1-propanol, derivatives and corresponding lower alkyl ethers and N-oxides of the present invention are used in the same range of amounts as threshold inhibitors in the scale inhibition method of the present invention, rather than as sequestering or chelating agents, although the compositions of the present invention have dispersant properties as well and significantly reduce the adherency of any scale deposit which is formed, facilitating its easy removal.

Scale-forming compounds can be prevented from precipitating by inactivating their cations with chelating or sequestering agents, so that the solubility of their reaction products is not exceeded. Generally, this requires many times as much chelating or sequestering agent as cation, since chelation is a stoichiometric reaction, and these amounts are not always desirable or economical. However, several decades ago, it was discovered that certain inorganic polyphosphates would prevent such precipitation when added in amounts far less than the concentrations needed for sequestering or chelating.

When a precipitation inhibitor is present in a potentially scale-forming system at a markedly lower concentration than that required for sequestering the scale-forming cation (stoichiometric), it is said to be present in "threshold" amounts. See, for example, Hatch and Rice, *Indust. Eng. Chem.*, 31, 51–53 (1939); Reitemeier and Buehrer, *J. Phys. Chem.*, 44 (5), 535–536 (1940); Fink and Richardson U.S. Pat. No. 2,358,222; and Hatch, U.S. Pat. No. 2,539,305.

Similarly, anionic and cationic polymers can be used as dispersants in accordance with methods known in the art, but the dosage levels necessary to achieve dispersion are in the range of 0.5–1.0% by weight of the system being treated, which is many orders of magnitude higher that the dosage levels used for the compositions of the present invention. Thus, it is a unique aspect of the present invention that it is possible to achieve essentially non-adherent scale using only threshold inhibitor dosage levels of the compositions of the present invention.

Recently, attention has been focused on controlling scaling under severe conditions, where conventional treatments such as those described above do not provide complete scale control. Current technology in scale control can be used to inhibit $CaCO_3$ scale up to 100 to 120 times calcite saturation, i.e., a water containing $Ca^{2+}$ and $CO_3^{2-}$ present at 100 times (100×) their solubility limit. However, what is desired are inhibitors effective in greater than 150× water, especially in greater than 250× water, i.e., where especially in greater than 300× water, i.e., where the calcite ions can be prevented from precipitating as calcium carbonate scale using substoichiometric amounts of an inhibitor. The compositions of the present invention are especially useful under severe conditions characterized by a calcite saturation level of 150× and above, especially 250× and above, and more especially 300× and above, as defined in the paragraph immediately below.

Severity of the scaling tendency of a water sample is measured using the saturation index, which may be derived in accordance with the following equation:

$$SI = \frac{[Ca^{2+}][CO_3^{2-}]}{K_{spCaCO_3}}$$

where SI is the saturation index for calcium carbonate, $[Ca^{2+}]$ is the concentration of free calcium ions, $[CO_3^{2-}]$ is the concentration of free carbonate ions, and $K_{spCaCO_3}$ is the conditional solubility product constant for $CaCO_3$. All of the quantities on the right side of the above equation are adjusted for pH, temperature and ionic strength.

Calculation and use of the saturation index, and generation of the data from which it is derived, are matters within the skill of the art. See, for example, *Critical Stability Constants*, Vol. 4: "Inorganic Complexes", Smith & Mantell (1976), Plenum Press; and *Aquatic Chemistry*, Chap. 5, 2nd ed., Stumm & Morgan (1981), Wiley & Sons.

Another characteristic feature of the severe conditions under which the scale controlling compositions of the present invention are especially useful is high pH, i.e. a pH of 8.5 and higher, particularly a pH of 9 or 10 or even higher. A related feature of such severe conditions is high alkalinity.

One of the particular advantages of the scale inhibiting compositions of the present invention is the exceptional calcium tolerances which they exhibit. Calcium tolerance is a measure of a chemical compound's ability to remain soluble in the presence of calcium ions ($Ca^{2+}$). One of the parameters of scale control under severe conditions is pH. As pH increases, calcium tolerance decreases rapidly for traditional $CaCO_3$ threshold inhibitors, e.g., 1-hydroxy ethylidene 1,1-diphosphonic acid (HEDP) and amino tri(methylene phosphonic acid) (AMP). These inhibitors precipitate with calcium at alkaline pH's, rendering them useless as threshold scale inhibitors. While it is common practice to use an acid feed to the water of, e.g., a cooling tower system in order to lower pH and thus avoid the calcium tolerance problem for conventional inhibitors, the danger to handlers which such acid feeding poses makes it all the more important to find scale inhibitors which operate at high pH's.

An advantage of the scale inhibiting compositions of the present invention which are N-oxides is their ability to maintain a level of resistance to degradation by oxidizing biocides which is sufficient to ensure adequate scale inhibition at dosing levels within the ranges herein described. This is of particular importance in cooling systems such as those using cycled up cooling towers. Such systems maintain a large body of water for a considerable length of time exposed to the atmosphere under conditions which do not include sufficient aeration and exposure to sunlight to provide control of microbial, especially bacterial and fungal, growth. Unchecked, such microorganisms flourish and produce colonies extensive enough to give rise to problems of biofilm blockage of heat exchange surfaces, and clogging of the components of the water transporting apparatus used in operating the cooling system.

Such problems of unwanted microbial growth in a cooling system are usually solved by use of an oxidizing biocide, especially chlorine or bromine, since these are inexpensive, effective, and produce minimal environmental impact. However, as is well known, such oxidizing biocides also tend to degrade scale inhibitors containing a N,N-bis(phosphonomethylene) group, presumably by oxidative attack on the nitrogen atom of the group. It has been found that the N-oxides of the present invention offer significant resistance to such degradation; and they will continue to provide scale inhibition when dosed in accordance with the ranges set out herein.

It is also a surprising attribute of the compounds, including N-oxides of the present invention that, even though they provide unacceptably low scale inhibition with aqueous systems having normal conditions and scaling tendencies, they provide an unexpectedly high level of scale inhibition protection in aqueous systems characterized by the severe conditions of high pH, high calcite concentration, etc., and having severe scaling tendencies, as described in detail further herein. It was wholly unexpected that compounds having that attribute, would also provide resistance to degradation by oxidizing biocides as well, under the severe conditions and scaling tendencies just described.

2. Brief Description of the Prior Art

Early efforts to reduce scale formation in water-carrying systems employed compounds such as tannins, modified lignins, algins, and other similar materials. Chelating or sequestering agents have also been employed to prevent precipitation or crystallization of scale-forming calcium carbonate. Another type of agent which has been actively explored heretofore as a calcium carbonate scale inhibiting material is the threshold active inhibitor. Such materials are effective as scale inhibitors in amounts considerably less than that stoichiometrically required, and this amount, as already mentioned, is termed the threshold amount. Inorganic polyphosphates have long been used as such threshold active inhibitors. For examples of such materials, see Fink—U.S. Pat. No. 2,358,222; Hatch—U.S. Pat. No. 2,539,305; and Ralston U.S. Pat. No. 3,434,969. Certain water soluble polymers, including groups derived from acrylamide and acrylic acid have been used to condition water containing scale-forming calcium carbonate. For example, see U.S. Pat. Nos. 2,783,200; 3,514,476; 2,980,610; 3,285,886; 3,463,730; 3,518,204; 3,928,196; 3,965,027; and 4,936,987In particular, there has been employed anionic polyelectrolytes such as polyacrylates, polymaleic anhydrides, copolymers of acrylates and sulfonates, and polymers of sulfonated styrenes. See, for example, U.S. Pat. Nos. 4,640,793; 4,650,591; 4,457,847; and 4,671,888. However, when used as threshold alkaline earth metal scale inhibitors, large dosages of these polymers are required, which in turn increases operating costs.

While various polycarboxylates, including polyacrylic acid, have been used as scale inhibiting agents, as described above, no similar use has been made of polycationic agents, apparently because of the difference in electronic charge and the conventional theories of the mechanisms of action for polymeric threshold inhibitors and dispersants.

Neither the N,N-bis(phosphonomethyl)-2-amino-1-propanol and corresponding lower alkyl ethers and N-oxides of the type which comprise the active ingredient of the compositions of the present invention are known, nor is their use for the control of alkaline earth metal scale, particularly calcium carbonate scale, under severe conditions which include elevated pH and high calcium carbonate saturation levels, with enhanced resistance to degradation by oxidizing biocides. Nevertheless, other phosphonates of related structure are known in the art for scale inhibition use.

For example, U.S. Pat. No. 4,080,375 discloses methylene phosphonates of amino-terminated oxyalkylates for use as scale inhibitors, but these compositions are not the same as those of the present invention, nor is there any suggestion that such compositions would be useful under severe conditions as defined herein, where phosphonates such as HEDP and AMP give poor results. U.S. Pat. No. 4,931,189 discloses aminomethylene phosphonates for inhibiting oil field scale formation involving a high brine environment susceptible to gypsum or barite scale formation. Such use in no way suggests the control of scale under the severe conditions described herein under which the compositions and methods of the present invention operate with surprising success.

A particular phosphonate which has been marketed for scale control, but apparently not suggested for use under the severe conditions defined herein, is ethanolamine N,N-dimethylene phosphonic acid, sold under such trademarks as WAYPLEX 61-A and BRIQUEST 221-50A.

U.S. Pat. Nos. 4,973,744 and 5,069,798 disclose N,N-bis-phosphonomethyl 2-(hydroxyethoxy) ethylamines and their N-oxides useful as scale inhibitors, but there is no suggestion of the unique isopropyloxy compounds of the present invention, nor of their particular usefulness for controlling scale under severe conditions.

SUMMARY OF THE INVENTION

The present invention relates to a compound of the formula:

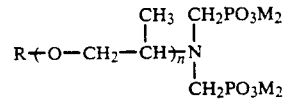

where n is an integer of from 1 to 3, inclusive; M is hydrogen or a suitable cation; and R is independently selected from hydrogen and $C_{1-4}$alkyl; and optionally, a compound of the above formula which is an N-oxide of the following formula:

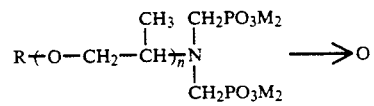

The present invention particularly relates to compounds of the above formulas wherein R is hydrogen, M is hydrogen, and n is 1, giving the compound N,N-bis(phosphonomethyl)-2-amino-1-propanol and its corresponding N-oxide; and wherein R is methyl, M is hydrogen, and n is 1, giving the compound N,N-bis(-phosphonomethyl)-1-methoxy-2-propanamine, and its corresponding N-oxide.

The present invention further relates to a composition useful as a deposit control agent to control the formation, deposition and adherency of scale imparting compounds in an aqueous system, comprising N,N-bis(-phosphonomethyl)-2-amino-1-propanol, derivatives and corresponding lower alkyl ethers thereof, of the following formula:

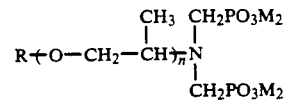

where n is an integer of from 1 to 3, inclusive; M is hydrogen or a suitable cation; and R is independently selected from hydrogen and $C_{1-4}$alkyl. Optionally, the compounds of the above formula may be N-oxides, in which event they have the following formula:

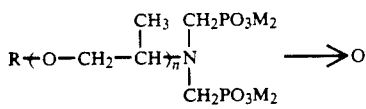

Preferably, R is hydrogen or methyl, M is hydrogen, and n is 1, giving the N,N-bis(phosphonomethyl)-2-amino-1-propanol and the corresponding methyl ether thereof.

The present invention also relates to a composition useful as a deposit control agent to control the formation, deposition and adherence of scale imparting compounds in an aqueous system comprising, in combination, N,N-bis(phosphonomethyl)-2-amino-1-propanol, derivatives and corresponding lower alkyl ethers and N-oxides of the formulas above, together with one or more members selected from the group consisting of homo- and copolymers including terpolymers comprising one or more of acrylamide (AM), acrylic acid (AA), 2-acrylamide-methyl propane sulfonic acid (AMPSA), methacrylic acid (MAA), itaconic acid (IA), polyether esters of acrylic and methacrylic acids and polyethers based on polyethyleneoxide and polypropyleneoxide and mixtures thereof, especially polyethylene glycol monomethacrylate (PGM), maleic anhydride (MA), maleic acid (MA), t-butyl acrylamide (TBAM), sodium styrene sulfonate (SSS), sodium vinyl sulfonate, hydroxy propyl acrylate, hydroxy propyl methacrylate, 3-allyloxy-2-hydroxy propane sulfonic acid (AHPS) sodium salt, and vinyl phosphonic acid, wherein the weight average molecular weight for such polymer additives is in the range of from about 500 to 250,000.

The present invention further relates to a method of inhibiting the formation, deposition and adherence of scale-forming salts in an aqueous system, comprising the step of adding to said system an amount sufficient to establish a concentration of from 1 to 100 mg/L of N,N-bis(phosphonomethyl)-2-amino-1-propanol, derivatives and corresponding lower alkyl ethers and N-oxides of the formula above. In particular, the present invention relates to such a method in which calcium carbonate is the scale-forming salt, the aqueous system comprises a cooling tower, and said compound is added to the aqueous system being treated in an amount sufficient to establish a concentration of from 10 to 50 mg/L.

The present invention further relates to a method of inhibiting the formation, deposition and adherence of scale-forming salts in an aqueous system, comprising the step of adding to said system an amount sufficient to establish a concentration of from 1 to 100 mg/L of a composition comprising N,N-bis(phosphonomethyl)-2-amino-1-propanol, derivatives, and corresponding lower alkyl ethers and N-oxides of the formula above, together with one or more members selected from the group consisting of: homo- and copolymers including terpolymers comprising one or more of acrylamide (AM), acrylic acid (AA), 2-acrylamide-methyl propane sulfonic acid (AMPSA), methacrylic acid (MAA), ethoxylated methacrylate, itaconic acid (IA), polyether esters of acrylic and methacrylic acids and polyethers based on polyethyleneoxide and polypropyleneoxide and mixtures thereof, especially polyethylene glycol monomethacrylate (PGM), maleic anhydride (MA), maleic acid (MA), t-butyl acrylamide (TBAM), sodium styrene sulfonate, sodium vinyl sulfonate, hydroxy propyl acrylate, hydroxy propyl methacrylate, 3-allyloxy-2-hydroxy propane sulfonic acid (AHPS), sodium salt, and vinyl phosphonic acid, wherein the weight average molecular weight for such polymer additives is in the range of from about 500 to 250,000. In particular, the present invention relates to such a method in which calcium carbonate is the scale-forming salt, the aqueous system comprises a cooling tower, said composition is added to the aqueous system being treated in an amount sufficient to establish a concentration of from 10 to 50 mg/L, and said polymer additive is a member selected from the group copolymers of the following weight percent compositions: 90/10 to 10/90 AA/AMPSA, preferably 75/25 and 60/40 AA/AMPSA, 100 AA, 75/25 SSS/MA, 33/33/34 AA/MAA/IA, 50/50 AA/AM, 70/20/10 AA/AMPSA/PGM-5, 10 and 20 (having 5, 10 and 20 repeating oxyethylene units, respectively), and AA/AMPSA/TBAM.

DETAILED DESCRIPTION OF THE INVENTION

The composition of the present invention useful as a deposit control agent to control the formation, deposition and adherency of scale imparting compounds in an aqueous system comprises N,N-bis(phosphonomethyl)-2-amino-1-propanol, derivatives, and corresponding lower alkyl ethers and N-oxides of the formula:

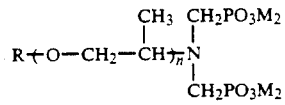

where n is an integer of from 1 to 3, inclusive; M is hydrogen or a suitable cation; and R is independently selected from hydrogen and $C_{1-4}$alkyl.

Optionally, the compounds of the above formula may be N-oxides, in which event they have the following formula:

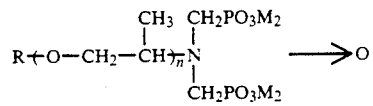

This key feature of the compounds of the present invention confers significant resistance to degradation by oxidizing biocides, presumably by preventing oxidative attack on the nitrogen atom of the group.

A preferred subclass of compositions of the above formula is that wherein M is hydrogen, n is from 1 to 3, more preferably 1, and R is hydrogen, methyl or ethyl, most preferably hydrogen or methyl. In order to obtain high levels of control of scale deposits, especially under the severe conditions defined herein, it has been found that there are certain essential components of the structure of the N,N-bis(phosphonomethyl)-2-amino-1-propanol, derivatives, and corresponding lower alkyl ethers and N-oxides of the present invention which are necessary to provide that performance, and thus clearly distinguish the compositions of the present invention from those of the prior art. For example, the N,N-bis(phosphonomethyl)amino portion of the structure is essential. Whether this group is present initially in the phosphonic acid form or as an alkali metal or other salt of the acid, has no critical bearing on the performance of the overall molecule. At the pH's under which the compositions of the present invention function, they are, and must be, in their ionized form. Thus, it is not critical whether "M" is hydrogen or a suitable cation, and the selection of an appropriate salt form is well within the skill of the art. Alkali metal salts are the most simple, and are preferred for that reason. Overall, however, it is preferred that M is hydrogen.

The most essential structural feature of the N,N-bis(phosphonomethyl)-2-amino-1-propanol, derivatives, and corresponding lower alkyl ethers and N-oxides useful in the compositions and methods of the present invention is the isopropyloxy group, or series of repeating isopropyloxy groups, up to 3 in number, which bridge the diphosphonomethylamino group and the terminal hydrogen (hydroxyl) or lower alkyl ether (lower alkoxyl) group:

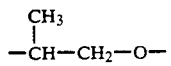

The isopropyloxy group has been found to be unique in providing enhanced scale inhibition activity under the severe conditions defined herein. For example, as demonstrated with data further below, when the N,N-bis(phosphonomethyl)-2-amino-1-propanol methyl ether of the present invention was compared to N,N-bis(phosphonomethyl)-2-amino-1-ethanol in an assay having such severe conditions, the scale inhibition performance of the compound of the present invention was found to be surprisingly better.

While it is preferred that there be only one isopropyloxy group, i.e., that n=1, it is within the scope of the present invention to have several repeating isopropyloxy groups present, up to three (3) in number, i.e., n=3. As the isopropyloxy groups increase in number, there is a gradual decrease in the scale inhibiting efficiency of the overall compound. However, all of these compounds continue to reflect the surprising improvement in performance attributable to the presence of the isopropyloxy group, whether one or more of such groups is present.

Another structural element of the N,N-bis(phosphonomethyl)-2-amino-1-propanol, derivatives, and corresponding lower alkyl ethers and N-oxides to be considered is the terminal hydroxyl or lower alkoxyl moiety: OR. As already indicated, R is preferably hydrogen, methyl or ethyl, more preferably hydrogen or methyl, and most preferably methyl. Where the lower alkyl ether is formed by propyl or butyl, there is again a gradual reduction in scale inhibition efficiency, but the compounds overall retain a surprising degree of effectiveness, and are thus within the scope of the present invention.

Finally, the optional structural feature of the N,N-bis(phosphonomethyl)-2-amino-1-propanol, derivatives, and corresponding lower alkyl ethers and N-oxides of the present invention must be considered, i.e., the N→0 moiety. As has already been described, this feature of the overall structure confers resistance to degradation by oxidizing biocides which is sufficient to ensure adequate scale inhibition at dosing levels within the ranges herein described.

The N,N-bis(phosphonomethyl)-2-amino-1-propanol, derivatives, and corresponding lower alkyl ethers and N-oxides of the compositions and methods of the present invention are prepared by phosphonomethylation of the appropriate primary amine which already contains the isopropyloxy moiety or moieties. Such primary amine starting materials and their method of preparation are well known. The phosphonomethylation of the primary amine is then carried out by a Mannich reaction such as that described in K. Moedritzer and R. Irani, *J. Organic Chem.* 31(5) 1603-7, "The Direct Synthesis of alpha-Aminomethyl Phosphonic Acids; Mannich-Type Reactions with Orthophosphorous Acid", May 1966. In a typical reaction, the primary amine is added to a mixture of phosphorous acid and water, and concentrated hydrochloric acid is then added slowly, after which the reaction mixture is heated to reflux with addition of aqueous formaldehyde.

Although the general structural formula employed herein indicates that the nitrogen atom is completely phosphonomethylated, as a practical matter, preparation of the N,N-bis(phosphonomethyl)-2-amino-1-propanol, derivatives, and corresponding lower alkyl ethers and N-oxides of the present invention, as described in detail further below, usually results in only about 80 to 90% phosphonomethylation. Other side products give N-substitution with H, $CH_3$, $CH_2OH$, etc. It is not practical, as a matter of simple production economics, however, to isolate and purify the completely phosphonomethylated compounds herein claimed, since the side products just described do not interfere with scale inhibition. Such side products, are consequently, usually allowed to remain.

The optional N-oxides of the compositions and methods of the present invention are prepared first by phosphonomethylation of the appropriate primary amine which already contains the polyoxypropylene moieties, as described above, followed by an oxidation step which provides the N-oxide moieties. Once the desired phosphonomethylated polyoxypropylene diamine has been prepared, the optional N-oxide final product of the present invention is then prepared by a step of oxidation, which may be accomplished, e.g., simply by adding hydrogen peroxide to a basic solution of the phosphonomethylated diamine and heating the reaction mixture, which gives high yields of the N-oxide final product. Of course, it is also possible to use other well known techniques for carrying out such a step of oxidation, and any number of these may be successfully employed.

When any of the N,N-bis(phosphonomethyl)-2-amino-1-propanol, derivatives, and corresponding lower alkyl ether and N-oxide compositions of the present invention are used to inhibit the precipitation, deposition, and adherence of scale-forming salts in an aqueous system, they can be effectively employed for that purpose when added in amounts sufficient to establish a concentration in said aqueous system of from 1 to 100 mg/L. Preferably, the amount added will be sufficient to establish a concentration of from 5 to 75 mg/L, and most preferably, the amount added will be sufficient to establish a concentration of from 10 to 50 mg/L of the composition. It is understood, however, that many factors, of the type which have been explained in detail with regard to the background to the present invention, will determine the actual amount of the N,N-bis(phosphonomethyl)-2-amino-1-propanol, derivatives, and corresponding lower alkyl ether and N-oxide compositions of the present invention which will be added to any particular aqueous system in order to achieve the maximum amount of inhibition of alkaline earth metal, especially calcium carbonate scale formation, deposition and adherence in that aqueous system. The calculation of those amounts is well within the skill of the artisan in this field.

When the N,N-bis(phosphonomethyl)-2-amino-1-propanol, derivatives, and corresponding lower alkyl ether and N-oxide compositions of the present invention are used in combination with one or more of the polymers recited further above, the amounts of that combination which must be added in order to inhibit the formation, deposition and adherence of scale-forming salts in an aqueous system, will as a general matter be within the ranges of amounts sufficient to establish the ranges of concentrations of the N,N-bis(phosphonomethyl)-2-amino-1-propanol, derivatives, and corresponding lower alkyl ethers and N-oxides used alone, as recited in detail above. Again, however, calculation of the actual amount is well within the skill of the art.

The phrases "inhibiting the precipitation" and "inhibiting the formation and deposition" are meant to include threshold inhibition, dispersion, solubilization, or particle size reduction. The phrases "inhibiting the adherence" and "increasing the non-adherence", are meant to define the formation of a scale deposit which is easily removed, e.g., by simple rinsing, i.e., a scale deposit which is not so firmly bonded to the surface to which it is attached that it cannot be removed by simple physical means as opposed to harsh mechanical or chemical treatment.

The phrase "scale-forming salts" is meant to include any of the scale-forming salts selected from the group consisting essentially of calcium carbonate, calcium phosphate, calcium phosphonate (including calcium hydroxyethylidene diphosphonic acid), and the corresponding magnesium salts.

The phrase "aqueous system" means commercial or industrial systems utilizing water and involving heat exchange surfaces, usually of metal, including cooling water systems including cooling towers, boiler water systems, desalination systems, gas scrubbers, and thermal conditioning equipment. Of particular importance are those systems which operate under severe conditions as detailed herein, including at least high pH and high calcite concentrations. Typical of such systems are cycled up cooling towers, reverse osmosis systems, sugar refining evaporators, and certain types of gas scrubbers.

The manner of addition of any particular N,N-bis(phosphonomethyl)-2-amino-1-propanol, derivative, or corresponding lower alkyl ether and N-oxide composition of the present invention, to an aqueous system will also be straightforward to a person of ordinary skill in this art. It may be added in liquid form by mechanical dispensers of known design. It may also be added in diluted liquid form. The N,N-bis(phosphonomethyl)-2-amino-1-propanol, derivative, or corresponding lower alkyl ether and N-oxide composition may also be combined with other chemical treatment agents for dispensing to the aqueous system; and these in combination may be dispensed in liquid form.

In the embodiments of the present invention described herein, it has been contemplated that, as a practical matter, only a single N,N-bis(phosphonomethyl)-2-amino-1-propanol, derivative, or corresponding lower alkyl ether and N-oxide composition of those described above would be used for the purpose of inhibiting scale. Of course, if would be possible to employ more than one such compound, and that forms a part of the present invention. However, it is also contemplated that one of these compositions not only could be combined, but preferably will be combined with one or more polyelectrolytes so as to provide an even more effective product for the inhibition of scale under the severe conditions described herein.

For example, there could be used in such a combination one or more members selected from the group consisting of homopolymers, copolymers and terpolymers comprising one or more monomers of acrylamide (AM), acrylic acid (AA), 2-acrylamide-methyl propane sulfonic acid (AMPSA), methacrylic acid (MAA), ethoxylated methacrylate, itaconic acid (IA), polyether esters of acrylic and methacrylic acids and polyethers based on polyethyleneoxide and polypropyleneoxide and mixtures thereof, especially polyethylene glycol monomethacrylate (PGM), maleic anhydride (MA), maleic acid (MA), t-butyl acrylamide (TBAM), sodium stryene sulfonate (SSS), sodium vinyl sulfonate, hydroxy propyl acrylate, hydroxy propyl methacrylate, 3-allyloxy-2-hydroxy propane sulfonic acid (AHPS), and vinyl phosphonic acid. Weight average molecular weights for such polymer additives should range from about 500 to 250,000.

For example, such compositions include the following weight percent compositions: 90/10 to 10/90 AA/AMPSA, preferably 75/25 and 60/40 AA/AMPSA. Other preferred polymer additives for use with the N,N-bis(phosphonomethyl)-2-amino-1-propanol, derivatives, and corresponding lower alkyl ethers and N-oxides of the present invention include 100 AA, 75/25 SSS/MA, 33/33/34 AA/MAA/IA, 50/50 AA/AM, 70/20/10 AA/AMPSA/PGM-5, 10 and 20 (having 5, 10 and 20 repeating oxyethylene units, respectively), (having 5 repeating oxyethylene units), and AA/AMPSA/TBAM.

Combinations using these polymers together with the N,N-bis(phosphonomethyl)-2-amino-1-propanol, derivative, or corresponding lower alkyl ether and N-oxide compositions of the present invention can increase the amount of scale control and deposit control which is achieved under the severe conditions described herein.

EXAMPLES OF PREFERRED EMBODIMENTS

The following examples are presented for the purpose of illustrating the present invention, but are not intended to be in any way a limitation thereof.

EXAMPLE 1

CaCO$_3$ Scale Inhibition at pH 9 and 300× Calcite Saturation-N,N-bis(Phosphonomethyl)-2-Amino-1-Propanol and Methyl Ether In order to demonstrate the improved scale inhibition performance of the N,N-bis(phosphonomethyl)-2-amino-1-propanol, derivatives and corresponding lower alkyl ethers and N-oxides used in the method of the present invention, and to compare that performance with that of other compounds under severe conditions, the following procedure was used:

PROCEDURE: Scaling water containing 250 mg/L of $CO_3^{-2}$ and 600 mg/L of alkalinity at a pH of 9.0 and 55° C. was used to evaluate scale inhibition performance of test solutions over a 24 hr period. Test solutions were analyzed by withdrawing 10 g of test solution and adding it to the appropriate container through a 0.2 μ filter, titrating for calcium, and calculating % inhibition by the Schwarzenbach method.

The results obtained are shown in the table of values below.

TABLE 1

| SAMPLE NO. | DESCRIPTION | % CaCO₃ SCALE INHIBITION | | |
|---|---|---|---|---|
| | | 20 ppm | 30 ppm | 50 ppm |
| 1 | $HOCH_2CH(CH_3)NZ_2$ | 98 | 98 | 96 |
| 221-50A | $HOCH_2CH_2NZ_2$ | 68 | 82 | 82 |
| 2 | $CH_3OCH_2CH(CH_3)NZ_2$ | 75 | 93 | 95 |
| 3 | $CH_3OCH_2CH_2O-[CH_2CH(CH_3)O]_9-CH_2CH(CH_3)NZ_2$ | 17 | 30 | 48 |

*where $Z = -CH_2PO_3H_2$; and 221-50A is sold under the trademark BRIQUEST.

The above results clearly show the surprising improvement in calcium carbonate scale inhibition under severe conditions when the isopropoxy, rather than ethoxy moiety is employed. The above results also demonstrate that a large number of repeating isopropoxy groups leads to a reduction in the level of scale inhibiting activity.

EXAMPLE 2

CaCO₃ Scale Inhibition at pH 9 and 300× Calcite Saturation-N,N-bis(Phosphonomethyl)-2-Amino-1-Propanol and Methyl Ether In Combination with Polyelectrolytes Following the test procedures described in Example 1 above, the N,N-bis(phosphonomethyl)-2-amino-1-propanol (Sample No. 1) and the methyl ether thereof (Sample No. 2) were evaluated in combination with two different polyelectrolytes. The % inhibition was calculated at 24 hours. The results of those evaluations revealed the unusually high degree of scale inhibition which can be achieved with such combinations under the severe conditions of the assay employed.

TABLE 2

% CaCO₃ Scale Inhibition with N,N-bis(Phosphonomethyl)-2-Amino-1-Propanol and the Methyl Ether thereof in Combination with Various Polyelectrolytes

| SAMPLE NO. | POLYELECTROLYTE | DOSAGE (ppm) | RATIOS OF POLYELECTROLYTE:PHOSPHONATE | |
|---|---|---|---|---|
| | | | 1:1 | 1:4 |
| 1 | 60/40 AA/AMPSA | 50 | 98 | 94 |
| 1 | 70/20/10 AA/AMPSA/PGM-5 | 50 | 97 | 94 |
| 2 | 60/40 AA/AMPSA | 50 | 55 | 62 |
| 2 | 70/20/10 AA/AMPSA/PGM-5 | 50 | 72 | 74 |

EXAMPLE 3

Preparation of N,N-bis(Phosphonomethyl)-2-Amino-1-Propanol $HOCH_2CH(CH_3)N(CH_2PO_3H_2)_2$ To a 500 mL 3-neck flask fitted with magnetic stirring, thermometer, condenser and addition funnel is added 22.53 g (0.30 mole) of 2-amino-1-propanol, 28.91 g of water, 70.29 g (0.60 mole) of 70% phosphorus acid and 50 mL of concentrated hydrochloric acid. This mix is heated to reflux and 97.39 g (1.20 moles) of 37% formaldehyde is added over a 30 minute period. The resulting solution is heated at reflux for 3 hours to complete the reaction. The solution is then reduced by 20% to yield an aqueous solution of 55.89%. Analysis of the ³¹P NMR spectra of this solution indicated the desired product.

EXAMPLE 4

Preparation of N,N-Bis(Phosphonomethyl)-2-Amino-1-Propanol Methyl Ether $CH_3OCH_2CH(CH_3)N(CH_2PO_3H_2)_2$ The primary amine 1-methoxy-2-propanamine, having the structural formula: $CH_3OCH_2CH(CH_3)NH_2$ (22.28 g, 0.25 mole) was added to a mixture of 70% phosphorous acid (58.57 g, 0.50 mole), 50 mL of concentrated hydrochloric acid, and deionized water (32.43 g) in a 250 mL 3-neck flask fitted with a condenser, a magnetic stirrer, a thermometer and an addition funnel. The reaction mixture was then heated to reflux, and there was then added 81.16 g (1.00 mole) of 37% aqueous formaldehyde (HCHO) over a period of about 25 min. The reaction mixture was then refluxed for an additional period of 3 hrs. to complete the reaction. The reaction mixture was then reduced by 20% to yield an aqueous solution of 46.4%. Analysis of the ³¹P NMR spectra of this solution indicated the desired product.

It has been found that the scale control performance of the N,N-bis(phosphonomethyl)-2-amino-1-propanol, derivatives, and corresponding lower alkyl ethers and N-oxides of the present invention depends to some extent, although not a very significant extent, on the variations in the process parameters described above. Best results are obtained, consequently, by employing the optimum conditions as outlined above.

What is claimed is:

1. A method of inhibiting the formation, deposition and adherence of scale forming salts including calcium carbonate in an aqueous system, containing water having $Ca^{+2}$ and $CO_3^{-2}$ present in greater than 150 times their solubility limit and a pH of at least 8.5, comprising the step of adding to said system an amount sufficient to establish a concentration of from 1 to 100 mg/L of a composition comprising N,N-bis(phosphonomethyl)-2-amino-1-propanol, derivatives, or corresponding lower alkyl ethers of the formula:

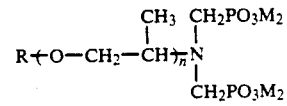

where n is an integer of from 1 to 3, inclusive; M is hydrogen or a suitable cation; and R is independently selected from hydrogen and $C_{1-4}$alkyl; and optionally, a compound of the above formula which is an N-oxide of the following formula:

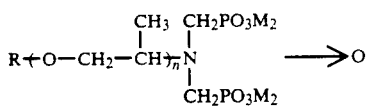

where n, M and R are as defined above.

2. A method according to claim 1 wherein calcium carbonate is the scale-forming salt and said propanol composition is added to the aqueous system being treated in an amount sufficient to establish a concentration of from 10 to 50 mg/L.

3. A method according to claim 2 wherein for the composition, M is hydrogen, R is hydrogen or methyl, and n is 1.

4. A method of inhibiting the formation, deposition and adherence of scale forming salts including calcium carbonate in an aqueous system, containing water having $Ca^{+2}$ and $CO_3^{-2}$ present in greater than 150 times their solubility limit and a pH of at least 8.5, comprising the step of adding to said system an amount sufficient to establish a concentration of from 1 to 100 mg/L of a composition comprising N,N-bis(phosphonomethyl)-2-amino-1-propanol, derivatives, and corresponding lower alkyl ethers of the following formula:

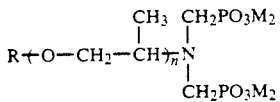

where n is an integer of from 1 to 3, inclusive; M is hydrogen or a suitable cation; and R is independently selected from hydrogen and $C_{1-4}$ alkyl; and optionally, a compound of the above formula which is an N-oxide of the following formula:

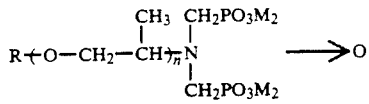

where n, M and R are as defined above;
together with one or more members selected from the group consisting of:

homopolymers, copolymers and terpolymers comprising one or more monomers of acrylamide (AM), acrylic acid (AA), 2-acrylamide-methyl propane sulfonic acid (AMPSA), methacrylic acid (MAA), ethoxylated methacrylate, itaconic acid (IA), polyether esters of acrylic and methacrylic acids and polyethers based on polyethyleneoxide and polypropyleneoxide and mixtures thereof, including polyethylene glycol monomethacrylate (PGM), maleic anhydride (MA), maleic acid (MA), t-butyl acrylamide (TBAM), sodium styrene sulfonate (SSS), sodium vinyl sulfonate, hydroxy propyl acrylate, hydroxy propyl methacrylate, 3-allyloxy-2-hydroxy propane sulfonic acid (AHPS), and vinyl phosphonic acid, wherein the weight average molecular weight for such polymer additives is in the range of from about 500 to 250,000.

5. A method according to claim 4 wherein for the phosphonate composition, M is hydrogen, R is hydrogen or methyl, and n is 1.

6. A method according to claim 4 wherein the polymer additive is selected from the group consisting of polyacrylic acid and the following weight percent composition 75/25 and 60/40 AA/AMPSA, 75/25 SSS/MA, 33/33/34 AA/MAA/IA, 50/50 AA/AM, 70/20/10 AA/AMPSA/PGM-5 (having 5 repeating oxyethylene units), and AA/AMPSA/TBAM.

7. A method according to claim 6 wherein calcium carbonate is the scale-forming salt and said propanol and said polymer additive are together added to the aqueous system being treated in an amount sufficient to establish a concentration of from 10 to 50 mg/L.

8. A method according to claim 7 wherein the aqueous system being treated is a cooling system.

* * * * *